United States Patent [19]
Wijesekera

[11] Patent Number: 5,502,211
[45] Date of Patent: Mar. 26, 1996

[54] SUBSTITUTED DIPYRROMETHANES AND THEIR PREPARATION

[75] Inventor: Tilak Wijesekera, Glen Mills, Pa.

[73] Assignee: Sun Company, Inc. (R&M), Philadelphia, Pa.

[21] Appl. No.: 143,261

[22] Filed: Oct. 26, 1993

[51] Int. Cl.⁶ .................................................. C07D 207/32
[52] U.S. Cl. ....................................................... 548/518
[58] Field of Search ............................................. 548/518

[56] References Cited

U.S. PATENT DOCUMENTS

| | | | |
|---|---|---|---|
| 4,892,941 | 1/1990 | Dolphin et al. | 540/145 |
| 4,900,871 | 2/1990 | Ellis et al. | 568/399 |
| 4,970,348 | 11/1990 | Ellis et al. | 568/399 |
| 5,077,394 | 12/1991 | Dolphin et al. | 530/505 |
| 5,118,886 | 6/1992 | Ellis et al. | 568/910 |
| 5,120,882 | 6/1992 | Ellis et al. | 568/910 |
| 5,124,449 | 6/1992 | Franck et al. | 540/472 |
| 5,241,062 | 8/1993 | Wijeserkera et al. | 540/145 |
| 5,360,880 | 11/1994 | Pashley et al. | 526/213 |

OTHER PUBLICATIONS

Chong et al., "The Chemistry of Pyrrolic Compounds VII. Synthesis of 5–5'-Diformyldipyrromethanes" Aust. J. Chem., 22, 229–238 (1969).

CA 113:230523d Formation . . . cations. Allen et al., p. 648, 1990.
CA 115:231951v Selective . . . meso–arylporphyrins. Ema et al., p. 917, 1991.
Tetrahedron Letters, vol. 32, No. 35, pp. 4529–4532, Selective . . . Meso–Arylporphyrins, 1991.
Ellis et al., "Halogen Substituent Effects on the Catalytic Activity of Iron Porphyrin Complexes for Selective Air–Oxidation of Alkanes in the Liquid Phase", *Cat. Lett.*, 3, 389 (1989).
Lyons et al., "Selective Low Temperature Hydroxylation of Isobutane By Molecular Oxygen Catalyzed by An Iron Perhaloporphyrin Complex", *Cat. Lett.*, 8, 45 (1991).

*Primary Examiner*—Joseph K. McKane
*Attorney, Agent, or Firm*—Q. Todd Dickinson; Stephen T. Falk

[57] ABSTRACT

New chemical compounds, bis(pyrrol-2-yl)halocarbylmethanes, also known as meso-halocarbyl dipyrromethanes, are made by recting pyrrole in either of two reaction schemes. Once such scheme converts pyrrole through an intermediate, a halocarbyl carbonyl pyrrole, to a [2-(1-hydroxyl-1-hydro-1-halocarbyl)pyrrole], and then converts the latter to the desired halocarbyldipyrromethane; the last step in this scheme is a novel and useful method in itself. The other such sequence converts pyrrole, by reaction with a halocarbyl aldehyde, directly to the desired halocarbyl dipyrromethane.

5 Claims, No Drawings

SUBSTITUTED DIPYRROMETHANES AND THEIR PREPARATION

The Government of the United States of America has rights in this invention pursuant to Cooperative Agreement No. DE-FC21-90MC26029 awarded by the U.S. Department of Energy.

BACKGROUND AND PRIOR ART

This invention provides new synthetic routes to 5,5'-unsubstituted-meso-halocarbyl dipyrromethanes which are useful precursors to linear di-, tri-, tetra-and polypyrrolic compounds, as well as cyclic polypyrrolic compounds such as porphyrins, azaporphyrins, expanded polypyrrolic macrocycles and their metal derivatives.

Cyclic polypyrrolic compounds such as porphyrins, azaporphyrins and expanded polypyrrolic compounds have found many uses both as their non-metallated free-base form as well as their metallated forms. Porphyrins in their nonmetallated form have been used as photosensitizers in the novel form of cancer treatment known as photodynamic therapy PDT ("Photodynamic Therapy: Basic Principles and Clinical Applications"; B. Henderson and T. J. Dougherty, Eds., Marcel Dekker, New York, 1992) while in their metallated form (particularly as Fe, Co, Mn, and Cr) have been used as catalysts for air oxidations of hydrocarbons (Ellis and Lyons, Catalysis Lett., 3, 389 1989; Lyons and Ellis, *Catalysis Lett.*, 8, 45 199; U.S. Pat. Nos. 4,900,871;4,970, 348) as well as degradation of lignin in the pulp and paper industry (U.S. Pat. Nos. 4,892,941; 5,077,394). Azaporphyrins (U.S. Pat. No. 5,124,449) and expanded polypyrrolic macrocycles (B. Ehrenberg, A. Lavi, Y. Nitzan, Z. Malik, H. Ladan, F. M. Johnson and J. L. Sessler, *Proc. SPIE-Int.Soc.Opt.Eng.* 1645 259, 1992; B. Franck, G. Fuelling, M. Gosmann, G. Knuebel, H. Mertes and D. Schroeder, *Proc. SPIE-Int. Soc. Opt. Eng.* 997 107 1989) have also found their use in PDT. In particular, the latter group of compounds, due to their ability to coordinate with larger paramagnetic metal ions such as Gd and Tc (due to the larger central cavity), have been examined as potential radiopharmaceuticals and paramagnetic contrast agents in magnetic resonance imaging MRI (J. L. Sessler, T.Murai, G.Hemmi, *Inorg. Chem.*, 28, 3390 1989). Variation of the type and position of the peripheral substituents of these macrocycles is known to change their photophysical, photochemical and electrochemical properties which in turn alter their activity.

Catalytic activity of porphyrins is known to increase with the introduction of electron-withdrawing substituents at all peripheral positions, beta as well as meso. Although some useful substituents can be introduced onto the macrocycle after its formation e.g. halogens; F, Cl or Br (U.S. Pat. Nos. 4,892,941; 4,970,348), nitro $NO_2$ (U.S. Pat. No. 5,120,882) and cyano CN (U.S. Pat. No. 5,118,886), certain groups e.g. hydrohalocarbyl, halocarbyl (Lindsey and Wagner, *J.Org.Chem.*, 54 828 1989) have to be introduced at the appropriate position of the precursor fragments during cyclization. Therefore if a porphyrin is to be modified to produce an efficient oxidation catalyst, it is preferable to have unsubstituted peripheral positions or have appropriate carbon bonded substituents (e.g. perhaloalkyl, perhaloaryl etc.) already in place.

Dipyrromethanes (1; see J. B. Paine in "The Porphyrins", D. Dolphin, Ed., *Academic Press*, New York, Vol. I, pages 101 and 163–234, 1978) are the most commonly used precursors for porphyrins. In addition, they are used to prepare tripyrrins and a,c-biladienes in the stepwise build-up of unsymmetrically substituted porphyrins, azaporphyrins and expanded polypyrrolic macrocycles. The use of dipyrromethanes for the synthesis of porphyrins containing electron-withdrawing groups in all peripheral positions has been limited by the inaccessibility of 5, 5'-unsubstituted dipyrromethanes (1; $R^1=R^7=H$) in which beta ($R^2, R^3, R^5, R^6$) and meso groups ($R^4$) are electron-withdrawing.

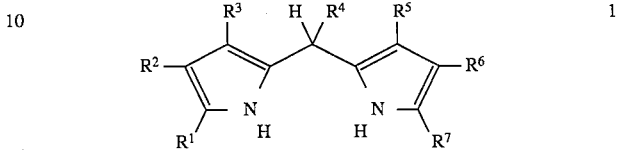

Dipyrromethanes carrying electron-withdrawing beta substituents are synthetically less useful since the presence of such groups renders the dipyrromethane highly unreactive at the 5,5' positions. However, if the beta positions are unsubstituted (R2=R3=R5=R6=H) and the meso position carries an electron-withdrawing substituent (e.g. R4=halohydrocarbyl or halocarbyl), the macrocycle derived from it will carry electron-withdrawing groups at the bridging carbons and will also have the beta positions available for subsequent functionalization with electron-withdrawing substituents (e.g. halogens).

Treibs and Jacob, "Benzoylierung in der Pyrrol-Reihe, II", *Liebigs Ann. Chem*, 733 27 1970 disclose reaction of benzoyl chloride with alkylpyrroles to give dibenzoyl-α-methylene pyrrolines, with some β-acetylpyrroles to give benzoates of their enol forms and with α-carboxypyrroles to form mixed anhydrides.

Allen, Kwong-Chip, Lin, Nguyen and Tidwell, "Formation and reactivity of 1-pyrrolyl-2,2,2-trifluoroethyl cations", *Canad.J. Chem.*, 68, 1709 1990 disclose that reaction of 1-methylpyrrole with trifluoroacetic anhydride gives 1-methyl-2-trifluoroacetyl-pyrrole, which is then reduced to the alcohol, which is then in turn converted to the p-nitrobenzoate.

Wijesekera and Wagner, "Synthetic Route to meso-Tetrahydrocarbyl or Substituted Hydrocarbyl Porphyrins and Derivatives", U.S. Pat. No. 5,241,062 disclose that reaction of pyrrole with trifluoroacetic anhydride gives 2-trifluoroacetylpyrrole, which is then reduced to the corresponding alcohol.

DESCRIPTION OF THE INVENTION

This invention provides two routes to 5,5'-unsubstituted dipyrromethanes (1; $R^1=R^7$) which may or may not be substituted at the beta positions, but carry meso-halocarbyl groups (for example: $R^4$=perfluoroalkyl) which have hitherto not been reported. With pyrrole itself as the starting material, one obtains dipyrromethanes with unsubstituted alpha and beta positions (1; $R^1=R^2=R^3=R^5=R^6=R^7=H$)

MULTISTEP METHOD OF SCHEME

In one embodiment of the invention, a multistep method for converting pyrroles to meso-halocarbyldipyrromethanes, referred to herein as Scheme 1 below, is provided which contains three steps. The first step in Scheme 1 is the reaction of pyrrole with a halo acid anhydride or halo acid chloride to produce a halocarbyl carbonyl pyrrole, having the formula, (Py)C(O)R, where (Py) is pyrrole, C(O) is carbonyl, and R is halocarbyl. The second step in Scheme 1 is the reaction of the halocarbyl carbonyl pyrrole produced in the first step with a reducing agent to produce a [2-(1-hydroxy-1-hydro-1-halocarbyl)pyrrole] having the formula, (Py)C(OH)R, where (Py) is pyrrole, C(OH) is hydroxyl-substituted carbon and R is halocarbyl. The third step is the reaction of the [2-(1-hydroxy-1-hydro-1-halocarbyl) pyrrole] produced in step 2 with pyrrole to produce a halocarbyl-substituted dipyrromethane, having the formula (Py)$_2$CHR where (Py) is pyrrole and R is halocarbyl. A typical example of such three-step synthesis is the reaction of pyrrole (2) with trifluoroacetic anhydride (3) to produce trifluoroacetylpyrrole (4), followed by the reaction of the latter with solid sodium borohydride to produce [2-(2-hydroxy-1,1,1-trifluoroethyl)pyrrole] (5), followed by the acid-catalyzed reaction of the latter with pyrrole to produce the dipyrromethane, bis-(pyrrol-2-yl) trifluoromethyl-methane (6). Any suitable reducing agent can be used in the second step. Sodium borohydride is preferred, but other suitable reducing agents can be used. A person skilled in the art can, in the light of the present specification, choose a suitable reducing agent, depending upon the presence or absence of substituents on the pyrrole ring.

Scheme 1

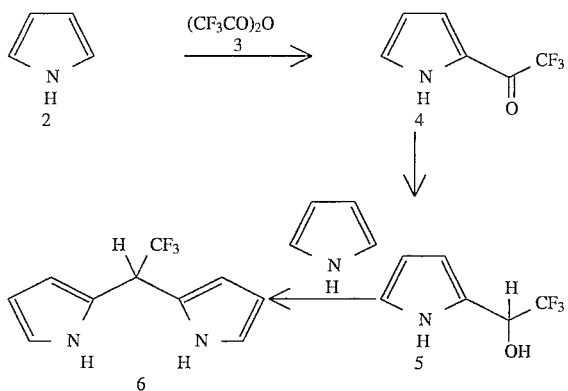

The first step in Scheme 1 provides a method of making halocarbyl carbonyl pyrroles, the second step a method of making [2-(1-hydroxy-1-hydro-1-halocarbyl)-pyrroles], and the third step, which is novel and useful in itself, a method of making novel halocarbyl dipyrromethanes.

MAKING HALOCARBYL CARBONYL PYRROLES

The first step of Scheme 1 comprises reacting a pyrrole 2 which is unsubstituted in the 2 and 5 positions with a halo acid anhydride or halo acid chloride to produce a halocarbyl carbonyl pyrrole. In this method, instead of pyrrole 2, as used in Example 1 above, pyrroles may be used which have substituents at the 3,4-positions, corresponding to the 3, 3', 4, 4' positions of 1 (see Paine above, page 166). Suitable such substituents include alkyl or substituted alkyl, aryl or substituted aryl. Instead of perfluoroacetic anhydride 3, as used in Example 1, other halocarbyl acid anhydrides or acid chlorides may be used, such as chloroacetic anhydride, chloroacetyl chloride, pentafluoropropionic anhydride. Instead of the trifluoroacetylpyrrole 4 produced in Example 1, other haloalkyl carbonyl pyrroles may be produced, such as trichloroacetylpyrrole and pentafluoropropionylpyrrole. The reaction may be carried out under suitable known conditions for reaction of pyrroles with acid anhydrides such as acetic anhydride.

MAKING [2-(1-HYDROXY-1-HYDRO-1-HALOCARBYL)-PYRROLES]

The second step of Scheme 1 above comprises reacting a halocarbyl carbonyl pyrrole as produced for example in the first step of Scheme 1 above with a reducing agent to produce such intermediate. Halocarbyl carbonyl pyrroles, as produced in the first step of Scheme 1 or from other sources, can be used as the starting material for the method. In this method, instead of 2-(2-hydroxy-1, 1, 1-trifluoro-ethyl)-pyrrole 5, as produced in the second step of Example 1, other hydroxy-substituted halo-alkylpyrroles may be produced such as 2-(2-hydroxy-1, 1,1-trichloroethyl)pyrrole. The reaction of the second step may be carried out under any suitable known conditions for converting oxygen atoms in carbonyl groups in substituted pyrrolic compounds to hydroxyl groups.

NOVEL METHOD OF MAKING HALOCARBYL DIPYRROMETHANES

The third step of Scheme 1 above provides in itself a novel method of making novel halocarbyl dipyrromethanes. The method comprises reacting a [2-(1-hydroxy-1-hydro-1-halocarbyl)pyrrole), as produced in the second step of Scheme 1 or from other sources, with a pyrrole to produce a 5,5'-unsubstituted-meso-halocarbyl dipyrromethane. In this method, instead of bis-(pyrrol-2-yl)trifluoromethyl-methane 6, as produced in the third step of Example 1, other haloalkyldipyrromethanes may be obtained depending on the halocarbyl anhydride or chloride used. Any suitable solvent may be employed instead of tetrahydrofuran, for example other ethers, alcohols such as ethanol, ketones etc., and any suitable acid catalyst such as hydrochloric acid, hydrobromic acid, solid acid catalysts such as Montmorillonite K-10 clays and other acid clays, and the like, the choice of the above being, in the light of the present specification, within the ability of the person skilled in the art.

ALTERNATIVE NOVEL METHOD OF MAKING HALOCARBYL DIPYRROMETHANES

Scheme 2 below provides another novel method of making 5,5'-unsubstituted-meso-halocarbyl dipyrromethanes. The method comprises reacting a pyrrole 2 with a halocarbyl aldehyde or its synthetic equivalent. In this method, instead of pyrrole 2 as used in Example 2 below, 3,4-disubstituted pyrroles may be used which have substituents, such as alkyl, substituted alkyl, aryl or substituted aryl at the positions corresponding to the 3,3', 4, 4' position of 1 Instead of the aldehydes used in Examples 2 and 3, compounds having the formula R'CHO may be used where R' is a halocarbyl group and the aldehyde group is a synthetic equivalent such as acetals hemiacetals or hydrates. The reaction may be carried out at suitable known conditions for the acid-catalyzed formation of dipyrromethanes by reaction of aldehydes with pyrroles. A solvent is preferably used, for example tetrahydrofuran, though other solvents as previously disclosed may also be used. Preferably, the reaction temperature is maintained by reflux of the reaction mixture, though other suitable temperatures may be used.

Scheme 2

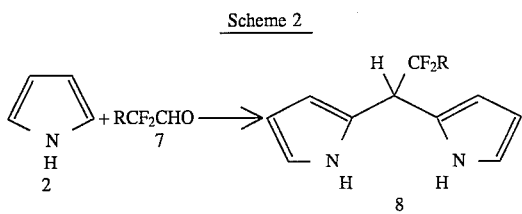

GENERAL REACTION SEQUENCES

Scheme 3 below depicts general reaction sequences for the synthesis of 5,5'-unsubstituted dipyrromethanes where R, in the aldehyde RCHO, is halocarbyl. The route from pyrrole through the intermediate 9, [2-(1-hydroxy-1-R-methyl) pyrrole], or (Py)CH(OH)R where (Py) is pyrrol-2-yl, to the dipyrromethane 10, bis-(pyrrol-2-yl)-R-methane, refers to Scheme 1 above. The route in which pyrrole 2 is converted directly to dipyrromethane be by reaction with aldehyde RCHO, refers to Scheme 2 above.

Scheme 3

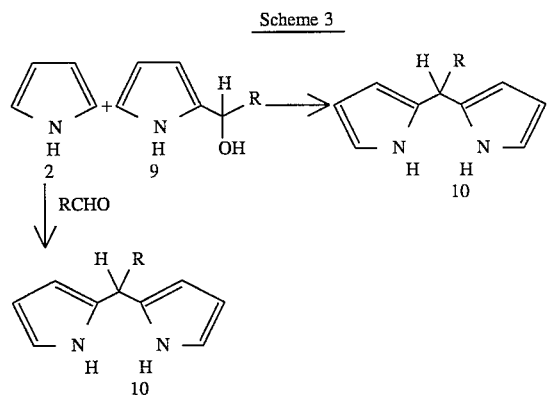

NEW CHEMICAL COMPOUNDS

The invention in one embodiment comprises new chemical compounds, namely bis-(pyrrol-2-yl)halocarbylmethanes. The number of the carbon atoms in the halocarbyl, for example haloalkyl, may be determined by a person skilled in the art in the light of the present specification, since the applicability of the invention in this respect is not limited to a particular range of carbon atoms. The synthesis and properties of bis-(pyrrol-2-yl)trifluoromethylmethane (8; R=F), and of bis- (pyrrol-2-yl) heptafluoroprop-1-yl-methane (8; R=CF$_3$CF$_2$) are given in Examples 2 and 3 below, respectively.

The following examples illustrate the invention:

EXAMPLE 1

Pyrrole (2) was reacted (over a 4 hour period), with an equimolar quantity of trifluoroacetic anhydride (3) in benzene under an inert atmosphere at 2°–3° C. The reaction mixture was diluted with water, the organic phase washed with aqueous sodium bicarbonate and water and the trifluoroacetylpyrrole 4 isolated in over 75% yield by evaporation of the solvent; m.p. 45°–46° C.; mass spectrum; m/z=163 (M$^+$).

Trifluoroacetylpyrrole 4 in methanol was reacted with solid sodium borohydride (in portions) at 0°–5° C. The reaction mixture was treated with a saturated solution of sodium bicarbonate and the product [2-(2-hydroxy-1,1,1-trifluoroethyl)pyrrole] (5) was extracted into ether. The ether solution was washed with aqueous sodium bicarbonate, water, dried and the product isolated in over 90% yield by evaporation of the solvent; mass spectrum; m/z=165 (M$^+$)

Equimolar quantities of pyrrole 2 and 2-(2-hydroxy-1,1,1-trifluoroethyl)pyrrole 5 (5mmol each) in tetrahydrofuran (30 mL) were refluxed with catalytic amounts of hydrochloric acid for 2 h under an inert atmosphere. GC analysis of the reaction mixture indicated the presence of the desired dipyrromethane, bis-(pyrrol-2-yl) trifluoro-methylmethane 6 in up to 65% yield. The pure product was isolated by neutralization of the acid, extraction into chloroform and chromatography. GCMS m/z; 214 (M$^+$, 55%); 145 (100%); $^1$H NMR ($\delta$, CDCl$_3$ at 7.24); 4.80 (q, 1H), 6.24 (m, 4H), 6.73 (s, 2H), 7.96 (bs, 2H).

EXAMPLE 2

Pyrrole (2; 150mmol) and trifluoroacetaldehyde (7; R=F, as the methyl hemiacetal, 75 mmol) in tetrahydrofuran (200 ml) are heated at reflux with concentrated hydrochloric acid. (4 ml) for 2 hours under an inert atmosphere. GC analysis of the reaction mixture indicated the presence of the desired dipyrromethane 8 (R=F; same as 6) in up to 80% yield. Neutralization of the acid followed by work up and chromatography gave the pure product in >60% isolated yield. By use of ethanol as solvent and optimization of work up procedure within the ability of the person skilled in the art in the light of the present specification, somewhat higher yields may be obtained. GCMS and $^1$H NMR of this material were identical to the material prepared by the method of Example 1.

EXAMPLE 3

Pyrrole (2; 50mmol) and heptafluorobutyraldehyde (7; R=CF$_3$CF$_2$, as the hydrate, 25 mmol) were condensed in tetrahydrofuran in the presence of acid catalyst as described above to give bis-(pyrrol-2-yl) heptafluoroprop- 1-yl-methane (8; R=CF$_3$CF$_2$) in >50% isolated yield. GCMS m/z; 314 (M$^+$, 22%), 145 (100%); $^1$H NMR ($\delta$, CDCl$_3$ at 7.24); 4.92 (t, 1H), 6.22 (d, 4H), 6.75 (s, 2H), 8.07 (bs, 2H).

Where "halocarbyl" is referred to in this specification, the term is understood to refer to hydrohalocarbyl or perhalocarbyl groups, where "perhalo" refers to complete substitution of halogen for hydrogen, or as nearly complete substitution as is reasonably attained under the circumstances.

The invention claimed is:
1. Bis (pyrrol-2-yl) perhalocarbylmethane compounds.
2. Compounds according to claim 1 wherein said perhalocarbyl is trifluoromethyl.
3. Bis (pyrrol-2-yl) perhalocarbylmethane compounds, wherein said perhalocarbyl is heptafluoropropyl.
4. Compounds according to claim 3, wherein said perhalocarbyl is perhaloaryl.
5. Compounds according to claim 4, wherein said perhaloaryl is perhalophenyl.

\* \* \* \* \*